United States Patent
Sahu et al.

(10) Patent No.: US 10,527,558 B2
(45) Date of Patent: *Jan. 7, 2020

(54) METHOD AND SYSTEM OF DETECTING FOREIGN MATERIALS WITHIN AN AGRICULTURAL PRODUCT STREAM

(71) Applicant: Altria Client Services LLC, Richmond, VA (US)

(72) Inventors: Amrita Sahu, Richmond, VA (US); Henry M. Dante, Midlothian, VA (US); Jerry W. Morris, Jetersville, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/266,530

(22) Filed: Feb. 4, 2019

(65) Prior Publication Data

US 2019/0170660 A1 Jun. 6, 2019

Related U.S. Application Data (63) Continuation of application No. 15/289,516, filed on Oct. 10, 2016, now Pat. No. 10,197,504.

(51) Int. Cl.
*G01N 21/94* (2006.01)
*G01N 21/359* (2014.01)
(Continued)

(52) U.S. Cl.
CPC ........... *G01N 21/94* (2013.01); *B07C 5/3422* (2013.01); *B07C 5/3427* (2013.01);
(Continued)

(58) Field of Classification Search
CPC .............. G01N 21/94; G01N 21/3563; G01N 202/8455; G01N 2201/10; G01N 2201/27
See application file for complete search history.

(56) References Cited

U.S. PATENT DOCUMENTS 3,854,586 A 12/1974 Perkins, III
3,939,983 A 2/1976 Asfour
(Continued)

FOREIGN PATENT DOCUMENTS

CN 101627832 A 1/2010
WO WO0058035 A1 10/2000
(Continued)

OTHER PUBLICATIONS

Bombick et al., "Evaluation of the Genotoxic and Cytotoxic Potential of Mainstream Whole Smoke and Smoke Condensate from a Cigarette Containing a Novel Carbon Filter", Fundamental and Applied Toxicology, vol. 39, pp. 11-17 (1997).

(Continued)

*Primary Examiner* — Christine S. Kim
(74) *Attorney, Agent, or Firm* — Buchanan Ingersoll & Rooney PC (57) ABSTRACT

Methods and systems for detecting foreign material within a product stream in real-time, involve illuminating a portion of the agricultural product stream with light spanning a wavelength range including or within near-infrared and/or shortwave infrared wavelengths; scanning a line of the illuminated agricultural product stream to acquire a hyperspectral image of the line, the hyperspectral image of the line having a width of a single pixel; processing the hyperspectral image of the scanned line to obtain spectrum data for one or more pixels of the hyperspectral image of the scanned line; comparing the obtained spectrum data of the one or more pixels to predetermined spectrum data to determine whether the obtained spectrum data is indicative of foreign material within the scanned line of the agricultural product stream.

17 Claims, 6 Drawing Sheets

(51) Int. Cl.
*G01N 21/85* (2006.01)
*B07C 5/342* (2006.01)
*G01N 21/3563* (2014.01)
*G01N 21/84* (2006.01)

(52) U.S. Cl.
CPC ....... *G01N 21/359* (2013.01); *G01N 21/3563* (2013.01); *G01N 21/85* (2013.01); *B07C 2501/009* (2013.01); *B07C 2501/0081* (2013.01); *G01N 2021/845* (2013.01); *G01N 2021/8455* (2013.01); *G01N 2021/8466* (2013.01); *G01N 2021/8592* (2013.01); *G01N 2201/10* (2013.01); *G01N 2201/127* (2013.01)

(56) References Cited

U.S. PATENT DOCUMENTS

| | | |
|---|---|---|
| 4,018,674 A | 4/1977 | Morris |
| 4,609,108 A | 9/1986 | Hristozov et al. |
| 4,778,987 A | 10/1988 | Saaski et al. |
| 4,836,224 A | 6/1989 | Lawson et al. |
| 4,924,883 A | 5/1990 | Perfetti et al. |
| 4,924,888 A | 5/1990 | Perfetti et al. |
| 5,056,537 A | 10/1991 | Brown et al. |
| 5,085,325 A | 2/1992 | Jones et al. |
| 5,159,942 A | 11/1992 | Brinkley et al. |
| 5,220,930 A | 6/1993 | Gentry |
| 5,301,694 A | 4/1994 | Raymond et al. |
| 5,360,023 A | 11/1994 | Blakley et al. |
| 5,476,108 A | 12/1995 | Dominguez et al. |
| 5,972,404 A | 10/1999 | van Lengerich |
| 6,400,833 B1 | 6/2002 | Richert |
| 6,421,126 B1 | 7/2002 | Kida et al. |
| 6,522,404 B2 | 2/2003 | Mikes et al. |
| 6,587,575 B1 | 7/2003 | Windham et al. |
| 6,637,598 B2 | 10/2003 | Takai et al. |
| 6,646,218 B1 | 11/2003 | Campbell et al. |
| 6,646,264 B1 | 11/2003 | Modiano et al. |
| 6,701,936 B2 | 3/2004 | Shafer et al. |
| 6,730,832 B1 | 5/2004 | Dominguez et al. |
| 6,819,798 B2 | 11/2004 | Gorin |
| 7,142,988 B1 | 11/2006 | Johnson |
| 7,227,148 B2 | 6/2007 | Sato et al. |
| 7,335,847 B2 | 2/2008 | Drewes et al. |
| 7,383,840 B2 | 6/2008 | Coleman |
| 7,411,682 B2 | 8/2008 | Moshe |
| 7,450,761 B2 | 11/2008 | Portigal et al. |
| 7,518,710 B2 | 4/2009 | Gao et al. |
| 8,564,769 B2 | 10/2013 | Zou et al. |
| 8,744,775 B2 | 6/2014 | Timmis et al. |
| 8,775,219 B2 | 7/2014 | Swanson et al. |
| 8,953,158 B2 | 2/2015 | Moshe et al. |
| 8,967,851 B1 | 3/2015 | Kemeny |
| 9,073,091 B2 | 7/2015 | Cadieux, Jr. |
| 2002/0008055 A1 | 1/2002 | Campbell et al. |
| 2003/0075193 A1 | 4/2003 | Li et al. |
| 2003/0131859 A1 | 7/2003 | Li et al. |
| 2004/0084056 A1 | 5/2004 | Lawson et al. |
| 2004/0146615 A1 | 7/2004 | McDonald et al. |
| 2004/0255965 A1 | 12/2004 | Perfetti et al. |
| 2005/0057263 A1 | 3/2005 | Moshe et al. |
| 2005/0066984 A1 | 3/2005 | Crooks et al. |
| 2005/0066986 A1 | 3/2005 | Nestor et al. |
| 2005/0211256 A1 | 9/2005 | Funke et al. |
| 2006/0292246 A1 | 12/2006 | Wu et al. |
| 2007/0265783 A1 | 11/2007 | Mound |
| 2009/0171591 A1 | 7/2009 | Timmis et al. |
| 2010/0290032 A1 | 11/2010 | Bugge |
| 2011/0125477 A1* | 5/2011 | Lightner ............ G05B 13/048 703/11 |
| 2011/0317001 A1 | 12/2011 | Massen |
| 2012/0214759 A1 | 8/2012 | Bruss et al. |
| 2012/0250025 A1 | 10/2012 | Moshe et al. |
| 2012/0321759 A1 | 12/2012 | Marinkovich et al. |
| 2013/0022250 A1 | 1/2013 | Nygaard et al. |
| 2013/0155402 A1 | 6/2013 | Walton et al. |
| 2013/0214162 A1 | 8/2013 | Treado et al. |
| 2014/0137877 A1 | 5/2014 | Deevi et al. |
| 2014/0197335 A1 | 7/2014 | Jayasooriya et al. |
| 2014/0327760 A1 | 11/2014 | Kurz et al. |
| 2015/0044098 A1 | 2/2015 | Smart et al. |
| 2015/0283586 A1 | 10/2015 | Dante et al. |
| 2015/0289557 A1 | 10/2015 | Deevi et al. |
| 2015/0347815 A1 | 12/2015 | Dante et al. |
| 2016/0252461 A1 | 9/2016 | Balthasar et al. |

FOREIGN PATENT DOCUMENTS

| | | |
|---|---|---|
| WO | WO0237990 A2 | 5/2002 |
| WO | WO2007041755 A1 | 4/2007 |
| WO | WO2007099540 A2 | 9/2007 |
| WO | WO2011027315 A1 | 3/2011 |
| WO | WO2014078858 A1 | 5/2014 |
| WO | WO2014078861 A1 | 5/2014 |
| WO | WO2014078862 A1 | 5/2014 |

OTHER PUBLICATIONS

Browne, "The Design of Cigarettes", 3.sup.rd Ed., pp. 43 (1990).

Davis et al., "Tobacco Production, Chemistry and Technology", Blackwell Science, pp. 346 and 440-451 (1999).

International Search Report of International Application No. PCT/US2013/070809 dated Mar. 7, 2014.

International Preliminary Report on Patentability for International Patent Application No. PCT/US2013/070809 dated Nov. 19, 2013.

International Preliminary Report on Patentability for International Patent Application No. PCT/US2013/070812 dated Nov. 19, 2013.

International Preliminary Report on Patentability for International Patent Application No. PCT/US2013/070814 dated Nov. 19, 2013.

International Preliminary Report on Patentability for International Patent Application No. IPRP PCT/IB2010/053952 dated Mar. 6, 2012.

International Preliminary Report on Patentability for International Patent Application No. PCT/US2013/070809 dated May 19, 2015.

International Preliminary Report on Patentability for International Patent Application No. PCT/US2013/070812 dated May 19, 2015.

International Preliminary Report on Patentability for International Patent Application No. IPRP PCT/IB2013/070814 dated May 19, 2015.

International Search Report of International Application No. PCT/US2013/070812 dated Mar. 7, 2014.

International Search Report of International Application No. PCT/US2013/070814 dated Mar. 7, 2014.

Luis Rodriguez-Cobo et al., "Raw Material Classification by Means of Hyperspectral Imaging and Hierarchical Temporal Memories", IEEE Sensors Journal, IEEE Service Center, New York, NY, US, vol. 12, No. 9, Sep. 1, 2012, ISSN:1530-437X, DOI:10.1109.2012.2202898.

P. Beatriz Garcia-Allende et al., "Hyperspectral Imaging for Diagnosis and Quality Control in Agri-food and Industrial Sectors", Proceedings of SPIE:, vol. 7726, Apr. 30, 2011, ISSN: 0277-786X, DOI: 10.1117.12.744506.

Pilar Beatriz Garice-Allende, "Hyperspectral Imaging Sustains Production-Process Competitiveness", Spie Newsroom, Jan. 1, 2010, DOI:10.11172.1201003.002681.

Robin Gruna et al., "Hyperspectral Imaging—From Laboratory to In-line Food Sorting", Cigar Workshop on Image Analysis in Agriculture, Jan. 1, 2010.

Russ Ouelette, "The Basics of Tobacco and Blending", pipesmagazine, Jul. 14, 2010, Retrieved from the Internet: URL:pipesmagazine.com/blog/put-that-in-your-pipe/the-basucs-of-tobacco-blending.

Timothy Kelman et al., "Classification of Chinese Tea Samples for Food Quality Control Using Hyperspectral Imaging", Hyperspectral Imaging Conference, Jan. 1, 2011.

Voges, "Tobacco Encyclopedia", Tobacco Journal International, pp. 44-45 (1984).

Headwall, Innovation in Spectral Sensing, Micro-Hyperspec, "Micro-Hyperspec Airborne Sensors", http://www.headwallphotonics.com/spectral-imaging/hyperspectral/micro-hyperspec, printed Jun. 1, 2017, 5 pages.

(56) References Cited

OTHER PUBLICATIONS

International Search Report and Written Opinion dated Dec. 21, 2017 in corresponding International Patent Application No. PCT/US17/53983 (12 pages).

* cited by examiner

METHOD AND SYSTEM OF DETECTING FOREIGN MATERIALS WITHIN AN AGRICULTURAL PRODUCT STREAM

CROSS REFERENCE TO RELATED APPLICATIONS

This application is a continuation application of U.S. patent application Ser. No. 15/289,516, filed Oct. 10, 2016, wherein the entire contents is hereby incorporated by reference.

FIELD OF THE INVENTION

The present disclosure relates to a method and system of detecting foreign material within an agricultural product stream. Disclosed herein is an on-line system and method for the detection and separation of unwanted materials and/or foreign matter from a product stream by employing hyperspectral imaging and advanced data processing and classification algorithms. Embodiments disclosed herein can be practiced with tobacco as well as other agricultural products, including tea, grapes, coffee, vegetables, fruit, nuts, breads, cereals, and other plant or animal parts.

BACKGROUND

Tobacco delivered for processing may occasionally contain foreign matter such as pieces of a container in which it is shipped and/or stored, bits of string and paper, foam, cardboard, foil, and/or other items. There is a need for methods and systems to remove foreign, non-tobacco related materials from tobacco prior to its incorporation into tobacco products. Further, there is a need for such methods and systems to be capable of conducting on-line detection of non-tobacco related materials, in real-time, without requirements for extensive computing resources or limited belt speeds.

SUMMARY OF SELECTED FEATURES

Disclosed herein is a method of detecting foreign material within an agricultural product stream in real-time. The method comprises illuminating a portion of the agricultural product stream with light spanning a wavelength range including or within near-infrared and/or shortwave infrared wavelengths. A line of the illuminated agricultural product stream is scanned to acquire a hyperspectral image of the line wherein the hyperspectral image of the line has a width of a single pixel. The hyperspectral image of the scanned line is processed to obtain spectrum data for one or more pixels of the hyperspectral image of the scanned line. The obtained spectrum data of the one or more pixels is compared to predetermined spectrum data to determine whether the obtained spectrum data is indicative of foreign material within the scanned line of the agricultural product stream.

Also disclosed herein is a system for detecting foreign material within an agricultural product stream in real-time. The system comprises an illumination device configured to illuminate a portion of the agricultural product stream at a wavelength range including or within near-infrared and/or shortwave infrared wavelengths. A hyperspectral imaging device is configured to scan a line of the illuminated agricultural product stream to acquire a hyperspectral image of the line wherein the hyperspectral image of the line has a width of a single pixel. A processor is configured to: process the hyperspectral image of the scanned line to obtain spectrum data for one or more pixels of the hyperspectral image of the scanned line, and compare the obtained spectrum data of the one or more pixels to predetermined spectrum data to determine whether the obtained spectrum data is indicative of foreign material within the scanned line of the agricultural product stream.

Further disclosed herein is a method of detecting foreign material within stationary agricultural product in real-time. The method comprises illuminating a portion of the stationary agricultural product with light spanning a wavelength range including or within near-infrared and/or shortwave infrared wavelengths. A hyperspectral imaging device is moved over a portion of the stationary agricultural product while the hyperspectral imagining device simultaneously scans a line of the illuminated stationary agricultural product to acquire a hyperspectral image of the line. The hyperspectral image of the line has a width of a single pixel. The hyperspectral image of the scanned line is processed to obtain spectrum data for one or more pixels of the hyperspectral image of the scanned line. The obtained spectrum data of the one or more pixels is compared to predetermined spectrum data to determine whether the obtained spectrum data is indicative of foreign material within the scanned line of the stationary agricultural product.

DETAILED DESCRIPTION

Disclosed herein are methods and systems for the detection and/or removal of foreign matter from a product stream, such as an agricultural product stream. By way of illustration, the systems and methods disclosed herein will be described for application during tobacco processing, but a system as disclosed herein could be applied during the processing of other products, such as other agricultural products. The detection and separation systems disclosed herein can be used in many processes and for consumer products which are susceptible to the presence of unwanted materials during a manufacturing process, such as, for example, in the growing, collection, processing and/or packaging of packaged consumer goods, such as food products, beverages, tipped and non-tipped cigars, cigarillos, snus and other smokeless tobacco products, smoking articles, electronic cigarettes, distilled products, pharmaceuticals, frozen foods and other comestibles, and the like. Further applications could include clothing, furniture, lumber, or any other manufactured or packaged product wherein an absence of non-product or foreign material is desired.

Tobacco may first be harvested at a farm, which in the case of tobacco for use in cigarette manufacturing or the production of moist smokeless tobacco (MST), may be harvested at least in part by machinery. Leaves of tobacco may be baled and received at a receiving station from the farm. Notably, the opportunity exists for the tobacco bale to come into contact with lubricated machinery at a receiving station as well as with other non-product related materials (i.e., foreign materials). The baled tobacco may be transferred to a stemmery wherein large stems may be removed by machines to produce de-stemmed tobacco. The de-stemmed tobacco can be packed into bales which are then stored for a suitable time period of up to several years. De-stemmed tobacco is then transferred to manufacturing centers, wherein various types of tobacco may be blended according to a predetermined recipe. The blended tobacco may be treated by adding various flavorants to provide a cased tobacco, which may be cut or shredded. Various other types of tobacco can be added to the blended tobacco including puffed tobacco, reconstituted tobacco, reclaimed tobacco, and the like, to provide a final product blend. The final product blend may be then fed to a make/pack machine, which includes a continuous tobacco rod making apparatus that makes tobacco rods from the final product blend. The tobacco rod may then be cut, optionally tipped, and packed, typically through the use of high-speed machinery.

As may be appreciated from the above description, in tobacco processing, tobacco comes into contact with machinery at many different points in the overall process, such as machinery used during the growing and harvesting operations on the farm, handling equipment at the receiving station or auction house, machinery in the stemmery, on conveyors, conditioners, cutters, silos, and other equipment at a manufacturing center. Additionally, as may be appreciated from the above description, various points exist during the process of tobacco product manufacturing in which non-product related material may be introduced to the product stream. Such non-product related material may include foreign matter such as foil, cellophane, warehouse tags, cardboard, foam, paper, or oil or other lubricant containing material.

Due to the inadvertent introduction of non-product material into a product stream during tobacco processing, there is a need for methods and systems that identify and remove non-product material from such product streams. The embodiments disclosed herein are generally focused on the manufacturing or processing of tobacco, blend components or samples, and the automated monitoring thereof by use of hyperspectral imaging technology. It should be understood that the embodiments disclosed herein could be applied to other domains encompassing, e.g., the manufacturing or processing of tea, fruits, during the production of fruit juices, grapes for the production of wines, as well as other agricultural products.

Hyperspectral imaging can be thought of as a combination of spectroscopy and imaging. In spectroscopy a spectra is collected at a single point. Spectra consist of a continuum of values that correspond to measurements at different wavelengths of light, which contain information about the chemical composition and material properties of a sample from which spectra are collected. In contrast, traditional cameras collect data including thousands of points. Data from each point or pixel contains one value (black and white image) or three values for a color image, corresponding to colors, red, green, and blue. Hyperspectral cameras combine the spectral resolution of spectroscopy and the spatial resolution of cameras. They can create images with, e.g., hundreds or thousands of pixels, that contain an array of values corresponding to light measurements at different wavelengths. Thus, the data at each pixel of a hyperspectral image includes a spectrum of wavelengths of light.

Hyperspectral imaging and analysis involves the scanning of an object while the object is exposed to electromagnetic radiation (e.g., in the form of light). When the object is illuminated, the electromagnetic radiation is affected by one or more of the physical, chemical, and/or biological species or components from which the object is comprised, by any of, or a combination of electromagnetic radiation absorption, diffusion, reflection, diffraction, scattering, and/or transmission mechanisms. Moreover, an object whose composition includes organic chemical species or components, ordinarily exhibits some degree of fluorescent and/or phosphorescent properties, when illuminated by some type of electromagnetic radiation or light, such as ultra-violet (UV), visible (VIS), or infrared (IR), types of light. The affected electromagnetic radiation, in the form of diffused, reflected, diffracted, scattered, and/or transmitted or emitted electromagnetic radiation of the object is directly and uniquely related to the physical, chemical, and/or biological properties of the object, in general, and of the chemical species or components making up the object, in particular. Thus, the data which may be acquired by a hyperspectral imaging device associated with a scanned object represents unique characteristics associated with the material of the object. The acquired data may be used to analyze and/or characterize the object for applications such as those described herein involving the identification and/or removal of foreign matter from a product or product stream.

By way of example and not limitation, techniques involving hyperspectral imaging and analysis and the implementation thereof in various stage of agricultural product processing is described in commonly-assigned U.S. application Ser. No. 14/084,213 to Deevi et al. (US PG-Pub. No. 2014/0137877); Ser. No. 14/443,986 to Dante et al. (US PG-Pub. No. 2015/0347815); Ser. No. 14/443,990 to Dante et al. (US PG-Pub. No. 2015/0283586); and Ser. No. 14/443,995 to Deevi et al. (US PG-Pub. No. 2015/0289557), the complete disclosures of which are expressly incorporated herein by reference in their entireties.

Embodiments of methods of detecting foreign material within agricultural products, such as tobacco products, disclosed herein may include the steps of: illuminating a portion of the agricultural product stream with light spanning a wavelength range including or within near-infrared and/or shortwave infrared wavelengths; scanning a line of the illuminated agricultural product stream to acquire a hyperspectral image of the line wherein the hyperspectral image of the line has a width of a single pixel; processing the hyperspectral image of the scanned line to obtain spectrum data for one or more pixels of the hyperspectral image of the scanned line; and comparing the obtained spectrum data of the one or more pixels to predetermined spectrum data to determine whether the obtained spectrum data is indicative of foreign material within the scanned line of the agricultural product stream.

In some embodiments, the method may further comprise a step of: determining, based upon the comparing step, the location of foreign material in the product stream and/or a step of determining, based upon the comparing step, that the scanned line of the agricultural product stream does not contain foreign material.

The agricultural product may be tobacco and may comprise tobacco leaves, shredded tobacco or other various forms of tobacco disclosed herein. The foreign material detected by the methods disclosed herein may comprise, e.g., one or more of: a foam, a cardboard, a plastic, a foil, a lubricant, or a paper. The predetermined spectrum data may be a calculated value based upon spectral data associated with, e.g., tobacco, foam, cardboard, plastic, foil, lubricant or paper.

The methods and systems disclosed herein may be implemented in connection with moving product streams (e.g., of tobacco or other agricultural product). In an embodiment, product may be positioned on a movable device that is operable to move the product so as to form a moving product stream. For example, product can be disposed on an upper surface of a conveyor belt such that when the conveyor belt is driven, the moving product stream moves past a hyperspectral imaging device (or instrument) that is operable to scan a portion of the moving product stream such that foreign matter in the moving product stream may be detected and subsequently removed. In an embodiment, the product stream may be continuously moving on the conveyor belt at speeds of up to 80 to 100 feet per minute.

In an embodiment, the hyperspectral imaging device is positioned in a location that enables a portion of the moving product stream to be scanned. The hyperspectral imaging device preferably operates in a range of about 900 nm to 1700 nm or about 900 nm to 2500 nm. In an embodiment, the hyperspectral imaging device can be a high speed camera having a frame rate of up to about 340 frames per second or greater. In an embodiment, hyperspectral images may be acquired with a line-scan hyperspectral imaging device wherein respective lines of the moving product stream are scanned by the hyperspectral imaging device as the product moves past the hyperspectral imaging device. In an embodiment, the portion of the moving agricultural product stream that the hyperspectral imaging device scans is a line of the product stream that is perpendicular to a direction in which the agricultural product stream is moving (e.g., a hyperspectral imaging device may scan a portion of an agricultural product stream perpendicular to the direction in which a conveyor belt is conveying the agricultural product). In an alternative embodiment, the hyperspectral imaging device can be a movable hyperspectral imaging device that is operable to scan stationary product as the hyperspectral imaging device moves across a portion of the product. In this embodiment, an illumination source can be configured to move with the hyperspectral imaging device.

In an embodiment, a moving product stream (i.e., product on a conveyor belt) is scanned line-by-line as the product stream passes the hyperspectral imaging device. The hyperspectral imaging device preferably captures one or more images of the product wherein each image captured by the hyperspectral imaging device is representative of a scanned line (i.e., a single row of pixels). Preferably, each image (or one or more pixels of an image) is processed in real-time such that non-product material and/or foreign material may be detected. By scanning and processing respective single lines that are captured in succession, and/or one or more pixels of the respective single lines captured in succession, redundant data gathering can be omitted. In this manner, processing time of the images can be reduced, and processing power can be conserved. Preferably, the methods for detection and/or analysis and/or removal of non-product material and/or foreign matter disclosed herein may be performed within systems having a continuously moving product stream, such as continuously moving product stream traveling on a conveyor belt at speeds of up to about 100 feet per minute, and preferably at speeds of about 80 to 100 feet per minute. In such embodiments, the detection of foreign matter and/or non-product material may be performed with resolutions, e.g., as low as 1 mm/pixel. In some embodiments, the hyperspectral imaging device may have a spectral resolution of around 5 nm. In some embodiments the hyperspectral imaging device may have a spatial resolution of around 0.25 inches. In some embodiments, the hyperspectral imaging device may be characterized by a frame rate of about 340 frames per second.

In some embodiments, the hyperspectral imaging device may record images with up to 67 spectral bands. In some embodiments, the hyperspectral imaging device may record images with up to 100 spectral bands. In some embodiments, the hyperspectral imaging device may record images with up to 150 spectral bands. In some embodiments, the hyperspectral imaging device may record images with more than 150 spectral bands. In some embodiments, the hyperspectral imaging device may record images with up to 320 spectral bands. In some embodiments, the hyperspectral imaging device may record images with up to 525 spectral bands. In some embodiments, the hyperspectral imaging device may record images with greater than 525 spectral bands.

In an embodiment, the hyperspectral imaging device implemented in the scanning of product may be aberration-corrected to account for and/or reduce or eliminate noise. Such aberration-correction may be accomplished via, e.g., systems and methods similar to those described in U.S. Pat. No. 6,522,404 to Mikes et al. or other methods and systems which will be apparent to those skilled in the art, or disclosed herein.

In some embodiments of methods as disclosed herein, a scanning step may include sensing a spectrum of light reflected, scattered, or emitted from product, such as a moving stream of the agricultural product, with at least one sensor wherein the scanning step is performed by a line-scan hyperspectral imaging device that includes the at least one sensor. In an embodiment, the at least one sensor is an Indium Gallium Arsenide (InGaAs) sensor. In an embodiment, the at least one sensor is operable to sense light in a wavelength range of about 900 nm to 1700 nm or about 900 nm to 2500 nm.

In some embodiments a pixel of a scanned image may have dimensions of around, e.g., 1.5 mm×1.5 mm. In some embodiments, a conveyor belt upon which product is conveyed may have a width of around 18 inches. In such embodiments, the hyperspectral imaging device may be configured to have a field of view of at least 18 inches, which is preferably directed perpendicularly to the direction in which the conveyor belt travels.

In some embodiments, multiple lines of product stream may be scanned individually, in a consecutive manner, as the product passes the hyperspectral imaging device. In some embodiments, each line of product stream is scanned and processed separately (e.g., multiple scanned lines are not processed to construct a hyperspectral image cube, etc.). Each scanned line may comprise a single row of pixels. The scanned line images may be acquired and processed as they are obtained (e.g., in real-time). For systems and methods disclosed herein, multiple scans of a single line of product are not required; however, multiple views or images of a single line of product may be obtained (i.e., scanned) based upon operator requirements. In some embodiments, each scanned line, or one or more pixels of a respective scanned line, may be separately analyzed to determine whether foreign material is detected in the portion of product material scanned by the hyperspectral imaging device. In some embodiments, a signal may be generated in response to detected foreign material. In some embodiments, detected foreign material can be mapped when the foreign material is detected in two or more consecutively scanned lines. In some embodiments, each consecutively scanned line, or one or more pixels thereof, may be analyzed to determine whether foreign material is detected wherein a signal that indicates a false positive may be generated when foreign material is detected in only a single scanned line. In an embodiment, this false positive signal may be overridden, such as when an analysis of the single scanned line meets or exceeds a predetermined threshold, for example, a predetermined threshold for a known foreign material.

In some embodiments, the multiple lines (e.g., portions) of product stream are scanned in a spatially consecutive manner. In some embodiments, a product stream may be scanned so that spatial gaps exist between consecutively scanned lines of product stream. For instance, a hyperspectral imaging device may be configured to scan a first line of a moving product stream and a second line of the moving product stream wherein a leading edge of the second scanned line (in the direction in which the product is traveling) is separated from a trailing edge of the first scanned line by a distance of about 15 mm or less, 10 mm or less, 5 mm or less 2 mm or less, or 1.5 mm or less.

In some embodiments, a step of processing the hyperspectral image of the scanned line to obtain spectrum data for the scanned line and/or one or more pixels thereof may comprise calibrating the scanned image (e.g., to remove dark values) and normalizing the image. In some embodiments, a step of processing the hyperspectral image of the scanned line to obtain spectrum data for the scanned line and/or one or more pixels thereof may comprise smoothing the images (e.g. to reduce or eliminate noise) using median filtering. For instance, smoothing can be performed by implementing the following equation to smooth the image: y[m,n]=median {x [i,j], (i,j)∈w), w represents neighborhood defined by the user, centered around location [m,n] in the image.

In some embodiments, a step of processing the hyperspectral image of the scanned line to obtain spectrum data for the scanned line and/or one or more pixels thereof may comprise calculating the Euclidean distance associated with one or more pixels of the scanned line. The Euclidean distance may be calculated by the following formula:

$$d(p, q) = \sqrt{\sum_{i=1}^{n} (q_i - p_i)^2},$$

wherein $p=(p_1, p_2 \ldots, p_n)$ and $q=(q_1, q_2 \ldots q_n)$ and p and q are two points in Euclidean n-space. In some embodiments, other classification techniques may be used such as Mahalanobis distance measure, Bhattacharya distance measure, spectral angle distance measure (SAM), maximum entropy classifier, curve fitting based on regression analysis, support vector machine (SVM), clustering techniques including k-means clustering, nearest neighbor clustering, or techniques based on neural network classifiers. In an embodiment, a combination of various data reduction and analysis techniques like principal component analysis, orthogonal decomposition, spectral mixture resolution, etc. could be used as a first step to reduce the dimensionality of the data and extract relevant features which could be used by a classifier. Preferably, Euclidean distance is implemented during processing to simplify processing of the scanned lines and/or one or more pixels of a scanned line. The Euclidean distance quickly provides calculated spectrum values that may be compared to predetermined spectrum data or threshold values such that the presence of foreign material may be accurately detected.

In some embodiments, the predetermined spectrum data may be determined by virtue of a data library, storing predetermined spectrum data associated with known materials or classes of materials (e.g., particular contaminants such as yellow foam, a specific type of lubricant, etc.; tobacco leaves; 95% pure tobacco leaves; etc.). In some embodiments, the predetermined spectrum data used for detecting foreign material is a threshold value for a material or class of materials. For instance, the spectrum data may correspond to a threshold value calculated for a given class of known foreign material, such as a foam, a foil, a paper, etc. (e.g., a contaminant known to commonly appear within a given product). As another example, the spectrum data may correspond to a threshold value calculated for a class of product material or a product material (e.g., uncontaminated tobacco leaves, 95% uncontaminated tobacco leaves, etc.). In some embodiments, the predetermined spectrum data or threshold value implemented according to methods and systems disclosed herein for determining whether product or a moving product stream contains contaminated product, and/or foreign material, may be determined by a process such as the following. The product material, class of product materials, known foreign material and/or class of foreign materials may be illuminated with near-infrared light spanning a particular wavelength (e.g., near-infrared, shortwave infrared, etc.). Such a wavelength may be similar to the wavelength of light used to illuminate product or a product stream in a method for detecting product material and/or foreign matter within that product or product stream. In some embodiments, the product and other known materials may be illuminated by light spanning a wavelength of 900 nm to 2500 nm, 900 nm to 1700 nm, or a wavelength within or comprising those ranges. In some preferred embodiments, the illuminating source may be a tungsten halogen light source.

The process may further involve separately scanning the product material, class of product materials, respective known foreign materials, and/or respective classes of known foreign materials to acquire hyperspectral reflectance image data for at least one of the respective product materials, class of product materials, known foreign materials, or class of known foreign materials. The process may further involve calculating, for at least one of the respective product materials, the class of product materials, the known foreign material, or the class of known foreign materials, a mean value of reflectance intensity, and based upon the one or more calculated mean values of reflectance intensity, determining the threshold value associated with at least one of the respective product material, the class of product materials, the known foreign material, or the class of known foreign materials.

To arrive at a threshold, hyperspectral images (e.g., hyperspectral reflectance images) of known materials may be acquired separately with a hyperspectral imaging device operating at a wavelength range similar to, or within, that of the light source illuminating the known materials. An image for a known material (e.g., yellow foam) may be acquired separately from an image for a second known material (e.g., pure tobacco leaves). The acquired images may be calibrated by removing dark values therefrom and/or normalized and/or subjected to a smoothing process to eliminate noise (e.g., via median filtering). Spectral feature values may be calculated which correspond to the known materials (or a known class of materials). For instance, a first value corresponding to a mean value of reflectance intensity may be calculated and associated with a yellow foam and a second value corresponding to a mean value of reflectance intensity may be calculated and associated with tobacco leaves. Spectral feature values may be acquired and stored within, e.g., a non-transitory computer-readable storage medium which may be accessed by system components (e.g., processing devices, etc.) implemented in carrying out a method for detecting and/or removing foreign and/or product matter from a product stream. Based upon the spectral feature values (e.g., mean reflectance intensity) of the known materials, a threshold for each known material or class of known materials may be calculated and, e.g., similarly stored within a computer-readable storage medium. The calculated threshold associated with each known material may be stored in a database in connection with the known material and subsequently accessed for implementation in a detection process such as those described herein.

Systems useful in connection with the methods of detection and removal described herein, may comprise the following components: an illumination source configured, e.g., to illuminate a portion of the product with light spanning a wavelength range within or comprising a near-infrared or shortwave infrared wavelength range; a hyperspectral imaging instrument configured to scan a line of the illuminated product and acquire a hyperspectral image of the line (i.e., a single row of pixels); and a processor configured to: process the hyperspectral image of the scanned line to obtain spectrum data for the image of the scanned line and/or one or more pixels of the image of the scanned line, analyze the obtained spectrum data (e.g., on a line-by-line basis, on the basis of one or several pixels of a line, etc.) to determine whether the obtained spectrum data is inconsistent with predetermined spectrum data for the product, and determine, when the spectrum data is inconsistent with the predetermined spectrum data for the product, that the scanned line of product comprises foreign matter.

In some embodiments, the processor may further be configured to calibrate the scanned image by removing dark values of the scanned image, and/or normalize the scanned image and/or smooth the scanned images to eliminate noise using, e.g., median filtering.

In some embodiments, the system may further comprise a foreign matter and/or product removal or separation device. In some embodiments, the processor may be further configured to generate an activation signal in response to a determination that a scanned line of product comprises foreign matter wherein the processor can transmit the activation signal to a removal device. In response to the activation signal, the removal device may be configured to separate or remove some or all of the product and/or foreign matter corresponding to the scanned line in which the foreign matter was detected. In some embodiments, the method may involve removal of the foreign material by a vacuum device and/or a forced fluid stream.

In some embodiments, the processor may, instead or in addition to generating and transmitting an activation signal, generate a display (e.g., of a graph representing values associated with the scanned line or a pixel of the scanned line, an image of the scanned line which may be enhanced to indicate materials displayed within the image, etc.) for conveying the determination to a user (e.g., via a user interface), create a model of the image of a scanned line, print results associated with the determination, etc.

The methods and systems disclosed herein offer certain advantages over known methods of detecting and analyzing products via hyperspectral imaging systems. For instance, embodiments disclosed herein do not require the implementation of end member extraction algorithms (e.g., to build spectral profiles, analyze scanned image data, etc.), the creation of a spectral library storing, e.g., full spectrum fingerprint data, the acquisition of dark and white references, etc. Thus, systems and methods disclosed herein offer significant computational savings over pre-existing hyperspectral imaging systems, enable methods to be performed more quickly (e.g., systems may be operated with high conveyor belt speeds), and may not require significant input energy or computational devices (e.g., a super computer), in contrast to known systems of hyperspectral imaging detection. Additionally, systems and methods disclosed herein may be performed in real-time, as image data is acquired on a line-by-line basis. Methods and systems disclosed herein may be operable to detect and remove foreign matter in a more efficient and quick manner than past methods of foreign matter detection. Systems and methods disclosed herein do not require the building of an image cube from multiple scanned lines or the storage of multiple images, thus, providing storage savings, in addition to processing resource savings, over known detection systems implementing hyperspectral imaging devices. For instance, an image acquired by a hyperspectral imaging device or camera may be thought of as comprising both spatial dimensions (e.g., M×N pixels) as well as a spectral dimension (e.g., comprised of a number of spectral bands, B). Thus, where a line image is acquired and analyzed separately from other lines acquired by the systems and methods disclosed herein, a width M of such an image may be assigned a value of 1.

Figure 1:
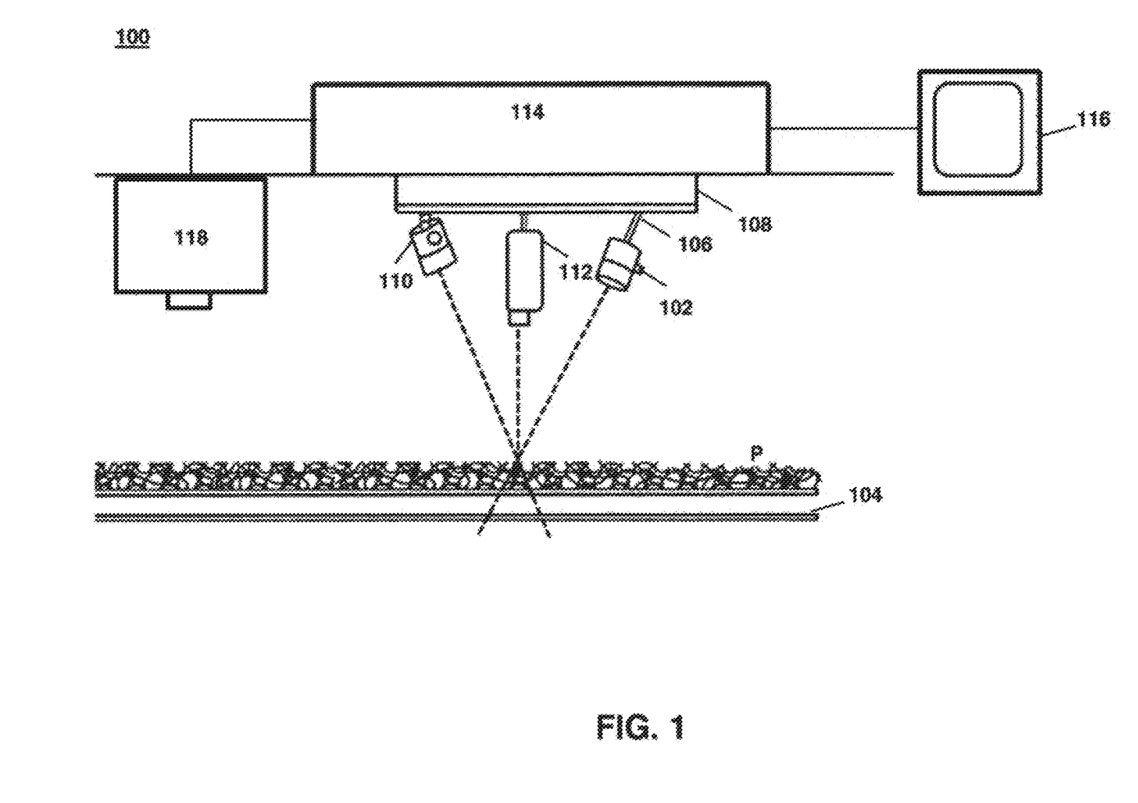
FIG. 1 is a schematic representation of a detection and separation system which may be implemented in connection with the present disclosure.

A schematic representing a basic hyperspectral imaging system which may be implemented for scanning agricultural product P is depicted in FIG. 1. The system 100 includes at least one light source 102 for illuminating agricultural product P. Agricultural product P is positioned on platform 104, which may be a fixed platform or a moving platform (e.g., a conveyer belt). As shown, the at least one light source 102 may be mounted on an arm 106 for positioning the at least one light source 102 relative to agricultural product P. Arm 106 may be mounted to frame 108 and may be fixed thereto or may be adjustable. Frame 108 may be moveable (e.g., so as to move over a portion of product P when the product is stationary) or may be a fixed structure (e.g., a wall or fixture). Light source 102 may be arranged in any of a number of positions within system 100, fixed or adjustable, so long as light source 102 is capable of illuminating product P. In some embodiments, additional light sources may be provided (e.g., second light source 110), which may be, e.g., fixed to frame 108. Alternatively, second light source 110 may be arranged in any number of positions within system 100, fixed or adjustable.

In some embodiments, light source 102 may be configured to provide a beam of light of different wavelengths, such as those in the visible light range, infrared range, ultraviolet range, or spanning one or more thereof. Light source 102 may be selected, e.g., according to a preselected wavelength range. Light source 102 may be, e.g., a tungsten light source, a xenon light source, a halogen light source, a mercury light source, a UV light source, and/or a combination thereof. In some embodiments, light source 102 may be a broad band light source veering the visible as well as the infrared spectral range, such as a tungsten halogen focused line light source.

In some embodiments, light source 102 may produce light within the near-infrared range, spanning a wavelength range from at least about 900 nm to about 2500 nm. In some embodiments, light source 102 may be configured to produce light spanning a wavelength range from at least about 900 nm to about 1700 nm. If desired, light source 102 may be filtered to reduce incident energy on scanned product. In embodiments having more than one light source, additional light sources, such as second light source 110 may be similar to or distinct from light source 102 (e.g., each light source may be of the tungsten halogen type; one of the light sources may be a halogen light whereas another may be a tungsten type; one light source may be fixed and another may be adjustable; the light sources may emit light of similar or distinct wavelengths; one or more light sources may emit light in a near infra-red range whereas an additional light source may emit light in the ultraviolet range, etc.). The number of light sources and type of light sources implemented in system 100 can be selected so as to provide the desired illumination energy.

In certain applications, the at least one light source 102 and/or the second light source 110 and/or additional light sources (not shown) may be positioned to minimize the angle of incidence of a beam of light with respect to agricultural product P. In some embodiments, system 100 or portions thereof may be enclosed within a structure (not shown) to provide a dark-room-type environment. In some embodiments, such as those implementing a near-infrared camera, fluorescent ambient light (e.g., visible light) will not affect the data collected by system 100. In some embodiments a line light source may be arranged so that two line lights are positioned along two sides of a product P or product stream provide illumination of a region of interest of product P or the product stream. In some embodiments, a light source may be positioned above and/or below the moving product stream.

Light source 102 and/or additional light sources, such as second light source 110 may illuminate only a region of product P to be scanned by a hyperspectral imaging device 112; however, in some embodiments, a larger region than that scanned by imaging device 112 may be illuminated by light source 102 and/or light source 110. In some embodiments light source 102 and/or additional light sources may be pulsed light sources. In some embodiments, light source 102 and/or additional light sources may be continuous light sources. In some embodiments one or more additional hyperspectral imaging devices (or other types of imaging devices) may be implemented to scan a same or different portion of product P as that scanned by imaging device 112.

In preferred embodiments, light source 102 and any additional sources of light implemented in system 100 are arranged so that the region to be scanned by hyperspectral imaging device 112 is uniformly illuminated and the image acquired by imaging device 112 is not saturated.

Hyperspectral imaging device 112 may be a commercially available hyperspectral imaging camera, such as those produced by Headwall Photonics of Fitchburg, Mass., those obtainable from Surface Optics Corporation of San Diego, Calif., or other companies, or may be custom built according to the needs of system 100. In a preferred embodiment, hyperspectral imaging device 112 is a near-infrared imaging device or a short wave infrared imaging device operating in a wavelength range of 900-1700 nm or 900-2500 nm, respectively.

In some embodiments, hyperspectral imaging device 112 may be configured to move relative to stationary product P. In preferred embodiments, product P may be positioned on movable platform 104 (e.g., a conveyor belt), and may move relative to hyperspectral imaging device 112 (e.g., conveyed past hyperspectral imaging device 112). In preferred embodiments, hyperspectral imaging device 112 is a line-scan hyperspectral imaging device, operable to acquire image data for a scanned line of a product stream of product P. In some embodiments, imaging device 112 may acquire data representative of a scanned line of product oriented across platform 104.

Hyperspectral imaging device 112 may include and/or be operably in communication with a processor 114. Processor 114 may be configured to receive scanned image data from imaging device 112 and process the received image data. In preferred embodiments the scanned image data, acquired by imaging device 112 and received by processor 114, comprises wavelength bands in the 900-1700 nm or 900-2500 nm wavelength range. Processor 114 may be configured to process received band data by employing one or more unique algorithms to determine the nature of the scanned product stream.

For instance, hyperspectral imaging device 112 may acquire hyperspectral image data of an illuminated line of a tobacco product stream. The tobacco product stream may be illuminated by light source 102 and/or second light source 110 operating within, e.g., the near-infrared wavelength range. Processor 114 may receive the hyperspectral image data from the hyperspectral imaging device 112 and may process the received image data according to, e.g., a predetermined algorithm. The hyperspectral image data may be processed by processor 114 on a pixel-by-pixel basis as the line of the product stream is scanned by imaging device 112. Thus, spectrum data corresponding to a pixel of the scanned line of the product stream may be determined. Alternatively or additionally, spectrum data corresponding to the scanned line may be acquired. Processor 114 may be configured to compare the spectrum data for the pixel and/or scanned line to a predetermined threshold value and, on the basis of such a comparison, determine whether the spectrum data for the pixel and/or scanned line is representative of tobacco or foreign (e.g., non-tobacco) matter. Hyperspectral imaging device 112 and processor 114 may be configured to obtain and process multiple scanned lines of a product stream on a line-by-line basis in real-time. That is, in embodiments of system 100, processor 114 is configured to detect foreign matter within a product stream without constructing an image cube of multiple scanned lines of the product stream.

Processor 114 may be in operable communication with a controller or control system via user interface 116. Interface 116 may include, e.g., a display and input device to enable a user to control system 100 or one or more components thereof. For instance, a user may provide data via interface 116 to processor 114 to be utilized in a determination as to acceptable product stream matter and unacceptable product stream matter.

In systems in which removal of scanned product is desired, processor 114 may be in operable communication with a product (or foreign matter) removal device 118. In systems wherein platform 104 is a movable platform, removal device 118 may receive a signal in response to a process performed by the processor 114 (e.g., analysis of a hyperspectral image of product stream) and may operate to remove some or all of a given portion of product stream based upon the received signal. Removal device 118 may remove product or non-product material by, e.g., vacuum or suction, physical removal via robotic arms, ejecting a fluid stream, etc. Removal device 118 may be positioned relative to product stream moving on platform 104 depending upon the type of removal mechanism employed. The activation mechanism for removal device 118 (e.g., a signal provided by processor 114 in response to analysis of acquired hyperspectral image data) may be based upon, e.g., the speed of movable platform 104 and distance between the position of the imaging device 112 and/or the position of product stream which is scanned by imaging device 112 and the removal device 118 and/or the position at which product or foreign matter is removed from the product stream by removal device 118.

To ensure accurate scanning, analysis, and/or removal of product stream, in the case of a movable platform 104, the platform (e.g., conveyor belt) speed may be tracked by, e.g., a sensor or triggering mechanism (e.g., a shaft encoder). The speed of the belt may be communicated to the processor 114 for use in various processes performed by system 100.

Figure 2:
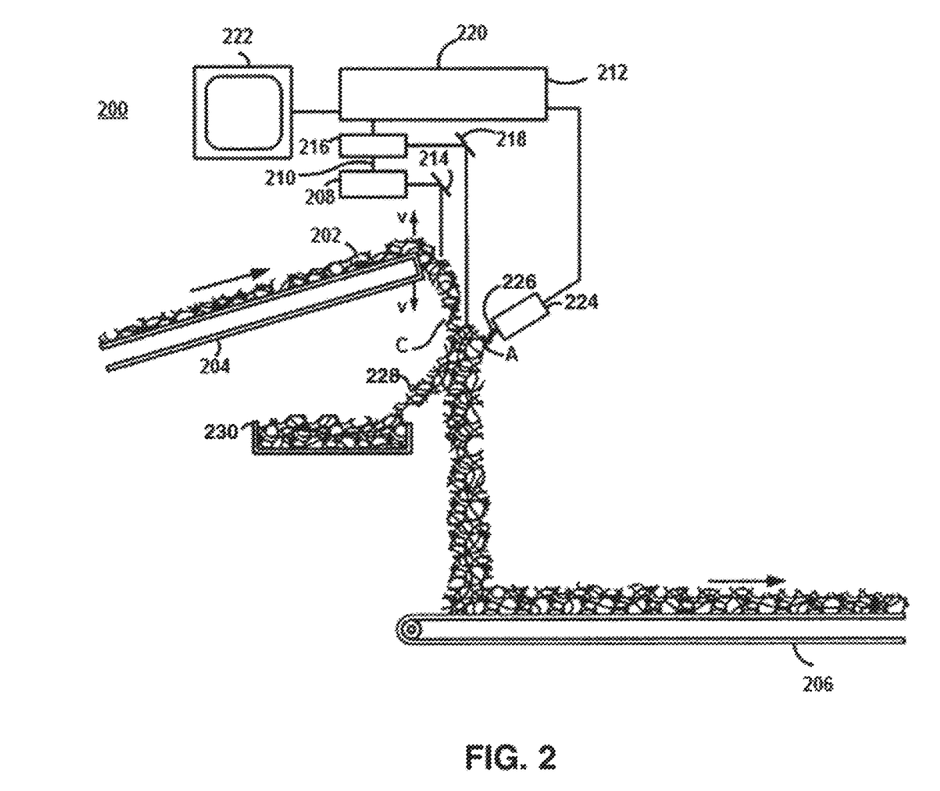
FIG. 2 depicts a detailed embodiment of a detection and separation system which may be implemented in connection with the present disclosure.

Referring now to FIG. 2, one possible embodiment of a detection and separation system 200, as disclosed herein, is shown schematically. Detection and separation system 200 may implement one or more components of system 100 (e.g., hyperspectral imaging device 112 may correspond to 216; light source 102 may correspond to 208; etc.). In operation, an agricultural product stream 202, which may be a tobacco stream, containing foreign material, such as foil, cellophane, warehouse tags, cardboard, foam, paper, or oil or other lubricant containing material, is delivered from a processing line by a conveyor 204. Conveyor 204 may be, e.g., a vibrating inclined conveyor which vibrates as shown by arrows v. In some embodiments, conveyor 204 ends above another conveyor 206, which can be, e.g., an ordinary conveyor belt. Conveyor 204 may be spaced vertically above conveyor 206 a sufficient distance to accommodate the remainder of system 200 as described herein. As product stream 202 reaches the end of conveyor 204, it drops under the influence of gravity in a cascade C to conveyor 106. In one embodiment, because conveyor 204 is inclined, the product stream does not have as great a horizontal velocity when it falls, so that cascade C does not have any significant front-to-back horizontal spread.

In alternative embodiments, detection and separation system 200 may include a single conveyor 204 for inspecting finished product, such as cigarettes, smokeless tobacco containers, SNUS pouches, etc., with product rejection, described in more detail below, taking place on the same conveyor. In such embodiments, conveyor 204 may be positioned horizontally or at an incline.

The detection and separation system 200 includes at least one light source 208 for providing a beam of light. As shown, the at least one light source 208 may be mounted on an arm 210 for positioning the at least one light source 208 in proximity to the product stream 202. In an embodiment, arm 210 may be mounted to structure 212 which may be, e.g., a cabinet, and arm 210 may be either fixed thereto or moveably position-able, as will be described herein. Additional light sources (not shown) may also be provided and mounted to the structure 212 or, optionally, to one or more additional arms (not shown), which in turn may be mounted to structure 212.

As shown in FIG. 2, the light from the at least one light source 208 may be directed toward the cascade C of the product stream 202 by the mirror 214. In alternative embodiments, light source 208 and/or additional light sources (not shown) may be positioned so as to directly illuminate product stream. In some embodiments, the light sources of system 200 may be positioned to minimize scattering effects. A hyperspectral image of product stream 202 may be acquired using hyperspectral imaging camera 216, which, in some embodiments, may receive light reflected by mirror 218. In alternative embodiments, the hyperspectral imaging camera 216 may receive light directly reflected from product stream 202.

In some embodiments, the at least one light source 208 and/or the additional light sources (not shown) may be positioned to minimize the angle of incidence of a beam of light with the agricultural product stream. In order to segregate ambient light form the light provided by system 200, walls (not shown) may be added to form an enclosure to provide a dark-room-like environment for a system 200.

A computer processing device may be included within system 200. For instance, a processor 220 may be mounted within structure 212. Processor 220 may be capable of rapidly handling system data and may be programmed, e.g., to compare received image data with threshold values as discussed above in connection with FIG. 1 and as further discussed herein. Processor 220 may be constituted by one or more conventional processors. Processor 220 operates to execute computer-readable steps, contained in program instructions, so as to control, e.g., various components of system 200 and/or system 200 as a whole. A device for providing uninterrupted power to processor 220 may be provided and, e.g., mounted within structure 212. A regulated power supply (not shown) may be provided to ensure that a tightly controlled source of power is supplied to system 200.

In some embodiments, system 200 is provided with a user interface 222 which enables an operator (not shown) to observe and/or control various operational aspects of system 200. User interface 222 is operably connected to processor 220 (e.g., via a networked computer system, etc.). User interface 222 may include a CRT or LCD panel for output display. User interface 222 may include a keyboard, touchscreen, mouse, joystick, or other known input means operable to enable an operator to input data into and/or control various aspects of system 200. User interface 222 may be located in close proximity to processor 220 and the product stream being analyzed within system 200 or may be situated at a remote location. Via user interface 222, an operator may, e.g., view representations of scanned portions of the product stream 202, e.g., in real-time as such portions are being processed and analyzed by system 200 or subsequent to scanning and analysis. In some embodiments, an operator may determine between acceptable product and unacceptable product (e.g., in real-time, prior to processing via configuring the processor 220, etc.) via user interface 222 (e.g., by viewing displayed data produced by processor 220 in response to scanning and analysis of product stream 202). In some embodiments, the determination between acceptable product and unacceptable product, the removal thereof, etc. is carried out via the processor 220 without operator input (e.g., automated).

In embodiments, when system 200 detects foreign material in product stream 202, processor 220 may produce a signal which may be communicated to ejector manifold 224, which is operably connected to processor 220 and which is positioned in downstream relation to the region illuminated by the at least one light 208. Ejector manifold 224 is in fluid transmission relation to the trajectory of the product stream 202. The ejector manifold 224 may include one or several ejector nozzles 226, which may be individually directed and controlled to selectively remove undesirable product material 228 from the product stream 202. The ejector nozzles 226 act as conduits for directing fluid pulses to dislodge or otherwise re-direct product material traveling in the trajectory of product stream 202. Individual ejector nozzles 226 contained in the ejector manifold 224 may be driven by a plurality of removal signals, which may be provided by processor 220, an operator via user interface 222, or via some other control system (not shown) in operable communication with ejector manifold 224.

In some embodiments, ejector nozzles 226 may be connected to a source of high pressure fluid. In some embodiments, the fluid is air at approximately 80 psi. In other embodiments, the fluid may be a gas or liquid other than air (e.g., steam, water, etc.). When one of the ejector nozzles 226 opens in response to a signal, a blast of air A is directed against that portion of cascade C in which the foreign material has been detected (e.g., by processor 220 via hyperspectral imaging data acquired by camera 216) to force that portion 228 of the product stream 202 and/or foreign material to fall into receptacle 230 for additional processing if necessary (e.g., manual sorting, removal by a conveyor to another system for processing, etc.). In the case usable product is forced into receptacle 230, it may be returned to the product processing line upstream or downstream of system 200, depending on whether or not rescanning of said usable product is desired.

As may be appreciated, system 200 may enable tobacco or other materials to be processed at greater rates than a system in which the tobacco or other materials are scanned on a standard belt conveyor. This is because when tobacco or other product material is optically scanned on a belt, it is desirable that the tobacco be in or close to a "monolayer" or single layer of particles, for all of the particles on the belt to be visible to the hyperspectral imaging camera 216. In embodiments of system 200, when the tobacco or other material falls in cascade C, relative vertical motion between the various particles of tobacco and foreign material is induced by the turbulence of the falling stream, so there is a greater probability that a particular piece of foreign material will be visible to hyperspectral imaging camera 216 at some point in its fall. Relative vertical motion also results if the foreign material is significantly lighter or heavier than the tobacco so that it has a greater or lesser air resistance as it falls. Relative vertical motion may be enhanced by the vibration of conveyor 204 which brings lighter material to the surface of the tobacco before it falls in cascade C, making the lighter material, which may represent foreign material, easier to detect, as in a monolayer. Alternative systems to the cascading system may be used in situations where a "monolayer" or similar type of layer is desired prior to scanning the product stream such as those which use brushes to separate product stream matter, etc.

The inclination of conveyor 204, in reducing the horizontal spread of cascade C as discussed above, also enhances relative vertical motion because the particles in cascade C have little or no horizontal velocity component. Any horizontal velocity component that a particle has when it falls off conveyor 204 is small because conveyor 204 is inclined, and air resistance quickly reduces the horizontal motion to near zero. The relative vertical motion allows a relatively thicker layer of tobacco or other material to be scanned, so that a greater volume can be scanned per unit of scanning area. Given a constant rate of area scanned per unit time, the increased volume scanned per unit area translates into a higher volume of tobacco or other material scanned per unit time.

Figure 3:
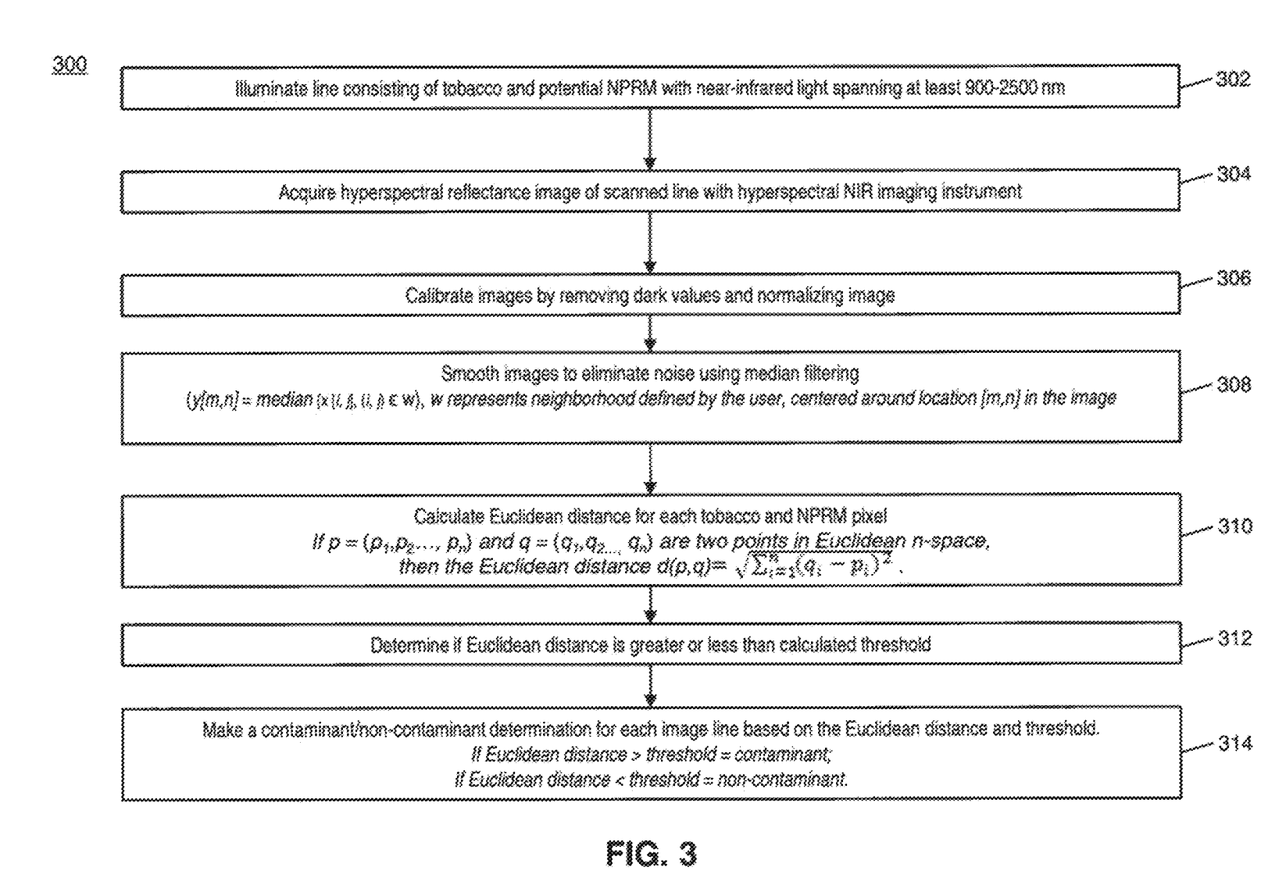
FIG. 3 presents, in a flow diagram, a testing or detection phase of a method for detection of foreign matter in a product stream (e.g., an agricultural product stream).

In operation, systems for detecting, analyzing and/or removing foreign matter (i.e., "non-product related materials" or "NPRM") from a product stream, such as those described in connection with systems 100 and 200, may operate by a process 300 such as that set forth in the flow chart of FIG. 3.

In step 302 of method 300, a line (e.g., of moving tobacco product stream intermixed with non-product related material) may be illuminated (e.g., by one or more light sources such as those discussed in connection with FIG. 1 and FIG. 2, above). The illuminated line may be illuminated with near-infrared light spanning at least from about 900 nm to about 2500 nm. In some embodiments, the line may be illuminated with at least near-infrared light spanning from about 900 nm to about 1700 nm.

In step 304, hyperspectral image data (e.g., a hyperspectral reflectance image) may be acquired. Hyperspectral imaging data may be obtained by hyperspectral imaging devices, such as device 112 of system 100 or device 216 of system 200. In embodiments, the imaging data may be obtained by a line-scan hyperspectral imaging instrument. In preferred embodiments, hyperspectral imaging data is obtained by a hyperspectral imaging instrument operating within the shortwave infrared (SWIR) or near infra-red (NIR) range. For instance the SWIR or NIR Micro-Hyperspec® Hyperspectral Sensors produced by Headwall Photonics, of Fitchburg, Mass. could be implemented in connection with method 300. In preferred embodiments, the image data acquired is single row of pixels that represents a line of the scanned product stream.

In step 306, obtained images may be calibrated (e.g., by a processing device) to remove dark values and normalize the images). If desired, calibration coefficients may be applied to compensate for fluctuations in operating conditions (e.g., light intensity, ambient conditions, etc.).

In step 308, obtained images may be smoothed (e.g., by a processing device) to eliminate noise. Smoothing of the images may be accomplished by, e.g., a median filtering process. Such as one represented by the following equation: (y[m,n]=median {x [i,j], (i,j)∈w), where w represents a neighborhood defined by, e.g., a user, centered around location [m,n] in the image.

In step 310, a value may be associated with one or more pixels of the scanned image data (e.g., with a pixel of an image representing a scanned line of product stream). Such a value may be calculated based upon a calculated Euclidean distance for each pixel. The Euclidean distance may be calculated by the following formula:

$$d(p, q) = \sqrt{\sum_{i=1}^{n} (q_i - p_i)^2},$$

wherein $p=(p_1, p_2 \ldots p_n)$ and $q=(q_1, q_2 \ldots q_n)$ and p and q are two points in Euclidean n-space. Each pixel of a scanned line may be associated with a corresponding calculated value. Alternatively, other classification techniques may be used such as Mahalanobis distance measure, Bhattacharya distance measure, spectral angle distance measure (SAM), maximum entropy classifier, curve fitting based on regression analysis, support vector machine (SVM), clustering techniques including k-means clustering, nearest neighbor clustering, or techniques based on neural network classifiers. In an embodiment, a combination of various data reduction and analysis techniques like principal component analysis, orthogonal decomposition, spectral mixture resolution, etc. could be used as a first step to reduce the dimensionality of the data and extract relevant features which could be used by a classifier.

In step 312, for each pixel associated with a corresponding calculated value, a determination may be made as to whether the value is greater than or less than a pre-determined threshold. The value (compared to the pre-determined threshold) for each pixel may be the Euclidean distance for that pixel, as described in step 310. In some embodiments, the scanned line may be associated with a corresponding calculated value and may be compared to a pre-determined threshold. In some embodiments values may be calculated and implemented within method 300 which are representative of multiple pixels or a scanned line as a whole rather than or in addition to values of individual pixels of a scanned line.

In step 314, the image of the line may be analyzed to determine whether the line contains foreign matter (e.g., non-tobacco related material). For instance, if the Euclidean distance associated with a pixel of the line is greater than the pre-determined threshold, a determination may be made that the pixel corresponds to foreign matter (i.e., contaminant or non-product related material). If the Euclidean distance associated with a pixel of the line is less than the threshold value, a determination may be made that the corresponding scanned matter is product material (e.g., uncontaminated tobacco). Alternatively, the pre-determined threshold may be selected so that, if the Euclidean distance associated with a pixel of the line is greater than the pre-determined threshold, the pixel may be determined to correspond to product matter, whereas a Euclidean distance associated with a pixel which is less than the pre-determined threshold may correspond to foreign matter. The threshold value may represent, e.g., a calculated data point, a distance from a calculated data point within which a material must fall to be considered similar to a material associated with a material corresponding to the data point, etc.

Steps 302 thru 314 may be carried out by various components of the systems 100 and 200, including but not limited to the processors, light sources and hyperspectral imaging devices disclosed therein, and other systems and system components similar thereto.

Figure 4:
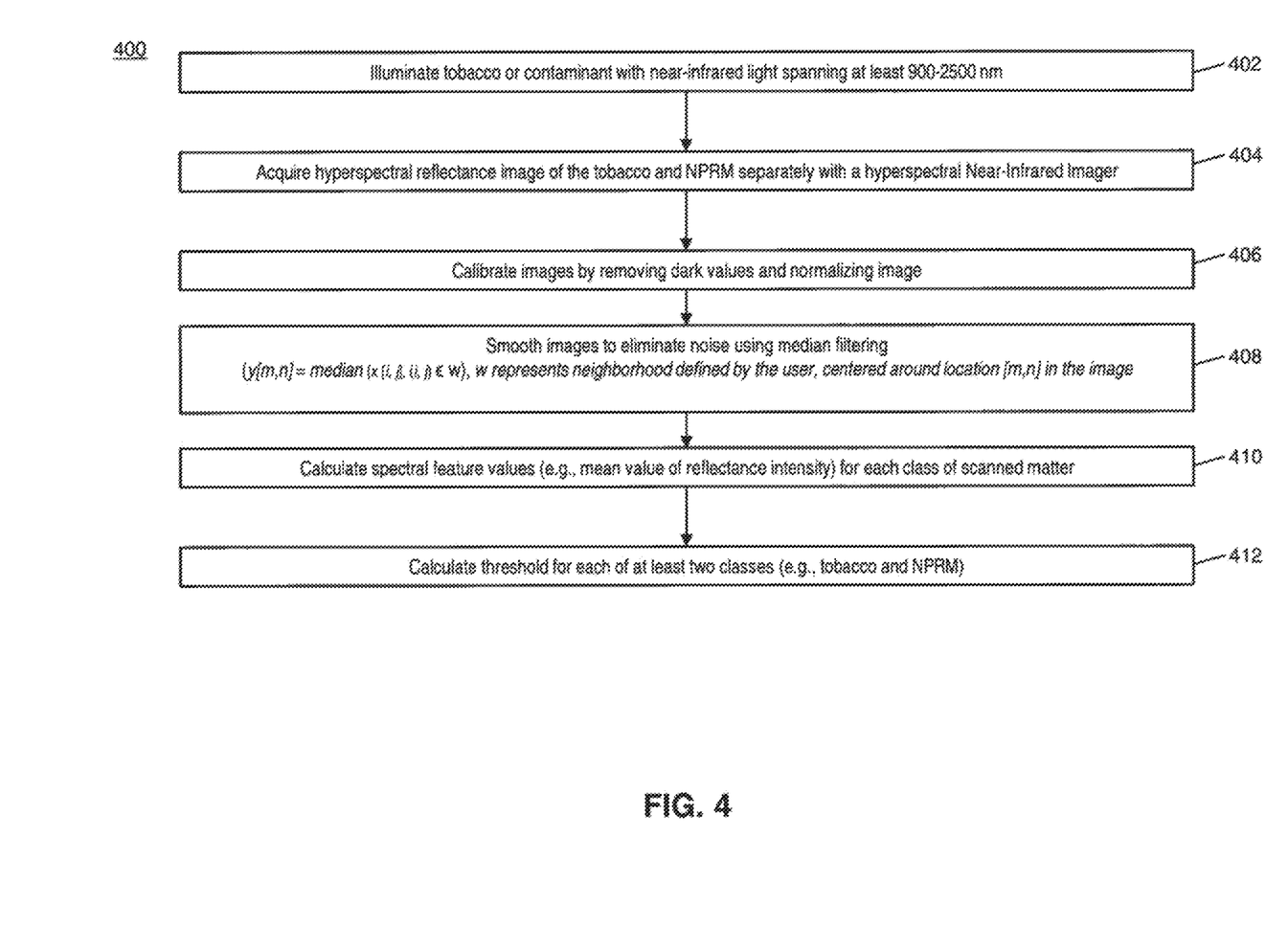
FIG. 4 presents, in a flow diagram, a training phase which may be implemented in connection with a method for detection of foreign matter in a product stream.

The pre-determined threshold value described in connection with method 300 may vary depending upon the application of method 300. Method 400 depicted in FIG. 4 provides one manner in which such a pre-determined threshold value may be calculated.

In step 402, known material (e.g., tobacco or contaminant material) may be illuminated with, e.g., near-infrared light spanning at least from about 900 nm to 2500 nm. In some embodiments, the material may be illuminated with light spanning at least 900 nm to 1700 nm. In alternative embodiments, other electromagnetic wavelength ranges (e.g., ultraviolet, visible light, infrared, etc.) may be implemented in methods 300 and/or 400 instead of or in addition to those in the near-infrared or shortwave infrared wavelength ranges.

In step 404, hyperspectral reflectance image data of the known material (e.g., product material or non-product related material/foreign matter) may be acquired with a hyperspectral imaging device, such as an NIR imaging device. The known material imaging data may be acquired separately from that acquired for other known materials. In some embodiments, the hyperspectral reflectance imaging device may be similar to or the same imaging device as that used to acquire image data of the product stream in method 300.

In step 406, the acquired images may be calibrated, e.g., by removing dark values and normalizing the image. In step 408, the images may be smoothed to reduce or eliminate noise, using a process such as median filtering (similar to that described in connection with step 308 of method 300).

In step 410, spectral feature values, e.g., a mean value of reflectance intensity, may be calculated for each known material and/or for a class of known material, for which image data is acquired. In step 412, threshold values may be determined for known materials and/or product material. Threshold values may be implemented in processes similar to those described herein (e.g., in method 300) and may be compared to scanned line or pixel data acquired by a real-time detection and removal system such as systems similar to those described herein.

Threshold values associated with known materials may be stored, e.g., in a non-transitory computer readable medium accessible by, e.g., systems such as those disclosed in FIG. 1 and FIG. 2, for implementation in a detection and/or removal process.

Figure 5:
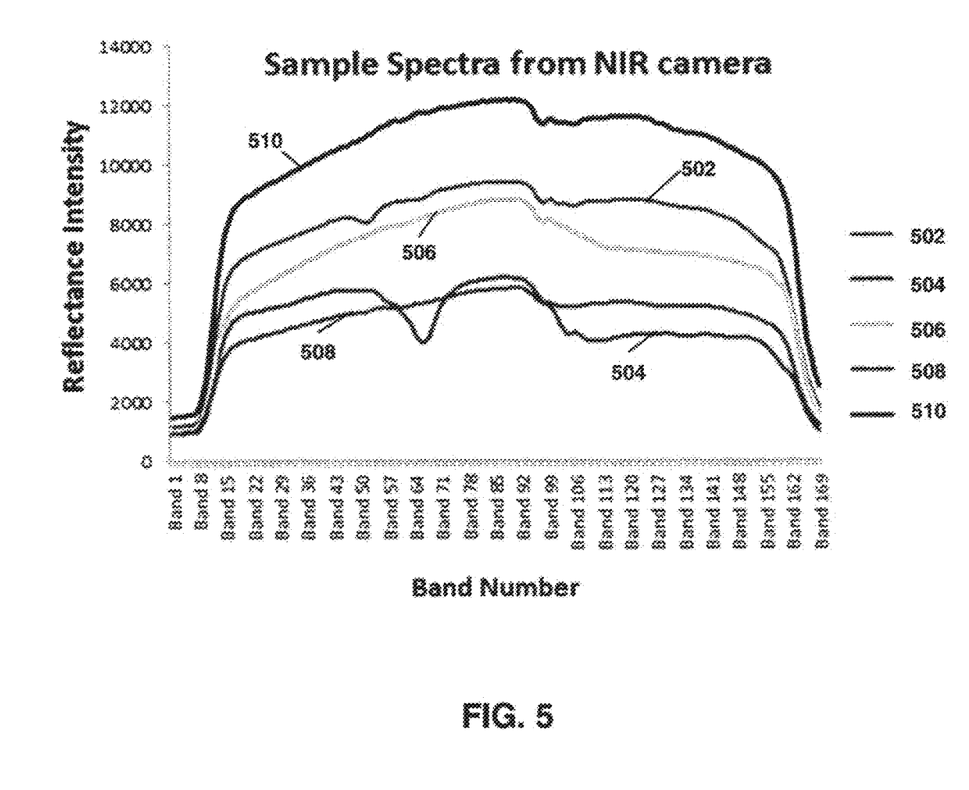
FIG. 5 sets forth a graph of sample spectra acquired by a hyperspectral near-infrared imaging instrument.

In FIG. 5, sample spectra from an NIR camera used in connection with methods and systems disclosed herein is presented in the form of a graph. The graph represents data collected with an NIR camera at a wavelength range of 900 nm to 1700 nm.

The various lines of the graph represent spectra associated with known materials. The line corresponding to 502 represents "white foam." The line corresponding to 504 represents spectrum data associated with a "belt" (e.g., such as a movable conveyor belt). The line corresponding to "tobacco" is labeled 506. The line corresponding to 508 represents spectrum data associated with "yellow foam." The line corresponding to 510 represents spectrum data corresponding to a "white reference."

As may be appreciated by one skilled in the art, yellow and white foam are known contaminants present in tobacco product streams. As can be understood from the spectra data presented in FIG. 5, the spectral signatures obtained by an NIR camera operating at a wavelength range of 900 nm to 1700 nm are extremely stable and almost rectangular throughout that wavelength range. The pronounced spectral difference illustrated between the known contaminants (e.g., 502 and 508) and the tobacco (506) enables methods and systems disclosed herein for detecting foreign matter in a product stream to be carried out accurately.

Figure 6:
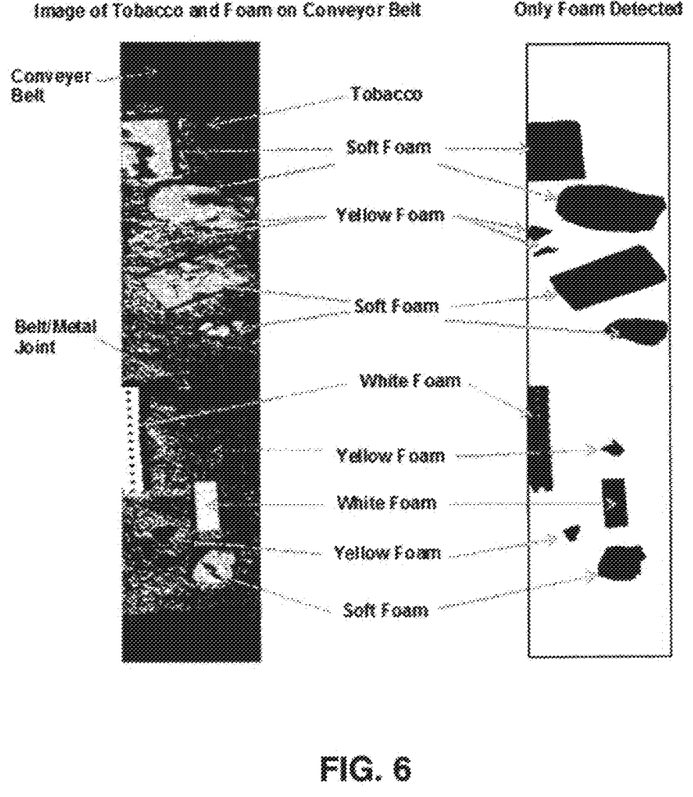
FIG. 6 depicts use of the systems and methods disclosed herein for detection of non-product related foam within a product stream of tobacco product.

FIG. 6 provides an example of results that may be produced by systems and methods described herein. As can be seen, a conveyor belt may convey product material (e.g., tobacco) along with contaminants/foreign matter (e.g., foam). Using methods and systems disclosed herein, the foam may be detected within the conveyed product stream. The foam may be detected by analyzing a hyperspectral image acquired of a scanned line of product to determine whether individual pixels (e.g., representative of 0.25 inches of contaminant material) should be identified as product or contaminant. The analysis may implement algorithms discussed in more detail herein. The analysis may result in the identification of only the contaminant material present in a scanned line of product. In some embodiments, results may be displayed in a manner similar to that of FIG. 6 (e.g., via a user interface). Where contaminant material is identified within a scanned line, as discussed herein, a signal may be generated and provided to a contaminant removal device which may remove contaminant material (or a line of product containing the contaminant material) from the product stream. This process may be carried out in real-time (e.g., without slowing the conveyor belt to remove the contaminated product material, etc.).

While the foregoing describes in detail systems and methods of detecting foreign material in product, or detecting and removing foreign material from product, with reference to specific embodiments thereof, it will be apparent to one skilled in the art that various changes and modifications and equivalents to the systems and methods disclosed herein may be employed, which do not materially depart from the spirit and scope of the invention.

We claim:

1. A method of detecting foreign material within an agricultural product stream in real-time, the method comprising:
   illuminating a portion of the agricultural product stream with light spanning a wavelength range including or within near-infrared and/or shortwave infrared wavelengths;
   scanning a line of the illuminated agricultural product stream to acquire a hyperspectral image of the line, the hyperspectral image of the line having a width of a single pixel;
   processing the hyperspectral image of the scanned line to obtain spectrum data for one or more pixels of the hyperspectral image of the scanned line; and
   comparing the obtained spectrum data of the one or more pixels to predetermined spectrum data to determine whether the obtained spectrum data is indicative of foreign material within the scanned line of the agricultural product stream without constructing a hyperspectral image cube.

2. The method of claim 1, wherein the scanned line of agricultural product stream is generally perpendicular to a direction in which the agricultural product stream is being moved.

3. The method of claim 1, wherein the predetermined spectrum data is a calculated value based upon spectral data associated with tobacco, foam, cardboard, plastic, foil, lubricant, paper, a sub-combination thereof, or a combination thereof.

4. The method of claim 1, further comprising a step of:
   determining, based upon the comparing step, the location of foreign material in the product stream; or
   determining, based upon the comparing step, that the scanned line of the agricultural product stream does not contain foreign material.

5. The method of claim 1, wherein the processing step comprises calculating the Euclidean distance associated with one or more pixels of the hyperspectral image of the scanned line, wherein the Euclidean distance is calculated by the formula:

$$d(p, q) = \sqrt{\sum_{i=1}^{n} (q_i - p_i)^2},$$

wherein $p=(p_1, p_2 \ldots, p_n)$ and $q=(q_1, q_2 \ldots, q_n)$ and p and q are two points in Euclidean n-space.

6. The method of claim 1, wherein the scanning step includes sensing a spectrum of light reflected, scattered, and/or emitted from the agricultural product stream with at least one sensor; wherein:
   (a) the scanning is performed by a line-scan hyperspectral imaging device that includes the at least one sensor;
   (b) the at least one sensor is an Indium Gallium Arsenide (InGaAs) sensor; and/or
   (c) the at least one sensor is operable to sense light in a range of about 900 nm to 1700 nm or about 900 nm to 2500 nm.

7. The method of claim 1, wherein:
   (a) the scanning is performed by a line-scan hyperspectral imaging device wherein the hyperspectral imaging device operates in the range of about 900 nm to 1700 nm or about 900 nm to 2500 nm; and/or
   (b) the illuminating is performed by a tungsten halogen light source.

8. The method of claim 1, wherein the agricultural product stream is a continuously moving agricultural product stream and is conveyed on a conveyer belt operating at a speed of about 80-100 ft/min.

9. The method of claim 1, wherein multiple lines of agricultural product stream are individually scanned consecutively, and the consecutively scanned lines are separately processed in-real time.

10. The method of claim 1, wherein the processing step comprises:
   calibrating the hyperspectral image of the scanned line by removing dark values of the hyperspectral image;
   normalizing the hyperspectral image of the scanned line; and
   smoothing the hyperspectral image of the scanned line to eliminate noise using median filtering.

11. The method of claim 1, wherein the predetermined spectrum data is a threshold value associated with a single product material, a class of product materials, a single known foreign material, a class of known foreign materials, a sub-combination thereof, or a combination thereof.

12. The method of claim 1 further comprising:
   generating an activation signal in response to determining that the scanned line of agricultural product stream comprises foreign material;
   transmitting the activation signal to a removal system; and
   removing the foreign material from the scanned line.

13. The method of claim 12, wherein the foreign material is removed by a vacuum device and/or a forced fluid stream.

14. A system for detecting foreign material within an agricultural product stream in real-time, the system comprising:
   an illumination device configured to illuminate a portion of the agricultural product stream at a wavelength range including or within near-infrared and/or shortwave infrared wavelengths;
   a hyperspectral imaging device configured to scan a line of the illuminated agricultural product stream to acquire a hyperspectral image of the line, the hyperspectral image of the line having a width of a single pixel; and
   a processor configured to:
   process the hyperspectral image of the scanned line to obtain spectrum data for one or more pixels of the hyperspectral image of the scanned line, and
   compare the obtained spectrum data of the one or more pixels to predetermined spectrum data to determine whether the obtained spectrum data is indicative of foreign material within the scanned line of the agricultural product stream without constructing a hyperspectral image cube.

15. The system of claim 14, wherein the processor is further configured to:
   determine, based upon the compared spectrum data, the location of foreign material in the product stream; or
   determine, based upon the compared spectrum data, that the scanned line of the agricultural product stream does not contain foreign material.

16. A non-transitory computer readable medium having instructions stored thereon, the instructions being configured to cause a processor to execute the steps of the method of claim 1.

17. A method of detecting foreign material within stationary agricultural product in real-time, the method comprising:

illuminating a portion of the stationary agricultural product with light spanning a wavelength range including or within near-infrared and/or shortwave infrared wavelengths;

moving a hyperspectral imaging device over a portion of the stationary agricultural product while simultaneously scanning a line of the illuminated stationary agricultural product to acquire a hyperspectral image of the line, the hyperspectral image of the line having a width of a single pixel;

processing the hyperspectral image of the scanned line to obtain spectrum data for one or more pixels of the hyperspectral image of the scanned line; and comparing the obtained spectrum data of the one or more pixels to predetermined spectrum data to determine whether the obtained spectrum data is indicative of foreign material within the scanned line of the stationary agricultural product without constructing a hyperspectral image cube.

* * * * *